US00PP25986P2

(12) United States Plant Patent
Falstad, III

(10) Patent No.: US PP25,986 P2
(45) Date of Patent: Oct. 13, 2015

(54) ***HIBISCUS* PLANT NAMED 'PLUM FANTASY'**

(50) Latin Name: ***Hibiscus* hybrid (L.)**
Varietal Denomination: Plum Fantasy

(71) Applicant: Walters Gardens, Inc., Zeeland, MI (US)

(72) Inventor: Clarence H. Falstad, III, Holland, MI (US)

(73) Assignee: Walters Gardens Inc, Zeeland, MI (US)

( * ) Notice: Subject to any disclaimer, the term of this patent is extended or adjusted under 35 U.S.C. 154(b) by 160 days.

(21) Appl. No.: 13/998,772

(22) Filed: Dec. 4, 2013

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — June Hwu

(57) ABSTRACT

A new and distinct cultivar of hardy herbaceous perennial *Hibiscus* hybrid plant named 'Plum Fantasy' comprising an upright dense branching, numerous flowers over a prolonged season having vibrant magenta-red overlapping petals and a darker red lustrous eye. The petals have a unique three-dimensional dimpling or puckering which helps resist strong wind, bright sun and harsh rain conditions. The foliage is dark-green, primarily heavily-dissected and tri-lobed.

1 Drawing Sheet

Botanical classification: *Hibiscus* hybrid (L.).
Variety denomination: 'Plum Fantasy'.

BACKGROUND AND ORIGIN OF THE PLANT

The present invention relates to the new and distinct hardy, herbaceous, *hibiscus* plant, *Hibiscus* 'Plum Fantasy' hybridized by Clarence H. Falstad, III in the summer of 2007 at a nursery in Zeeland, Mich. The new plant, originally labeled # F7-16-01, is from a cross between *Hibiscus* 'Summer Storm' U.S. Plant Pat. No. 20,443 (female pod parent) times the proprietary hybrid # 05-139-17 (not patented) (male pollen parent). Both parents have a complex mixture of species in them, most likely including the species: *moscheutos, coccineus* and *laevis* (formerly *militaris*). *Hibiscus* 'Plum Fantasy' was first asexually propagated in 2010 by both stem cuttings and sterile tissue culture at the same nursery in Zeeland, Mich. The resultant asexually propagated plants have been found to be stable and true to type in successive generations of asexual reproduction.

BRIEF SUMMARY OF THE PLANT

*Hibiscus* 'Plum Fantasy' differs from its parents as well as all other hardy herbaceous *hibiscus* known to the applicant in many traits. The foliage color of 'Plum Fantasy' is dark green with generally tri-lobed foliage. The most similar *hibiscus* in flower color known to the applicant is 'Sultry Kiss' U.S. Plant Pat. No. 22300, but the petals of the new plant are puckered three-dimensional in an unusual way and the color of 'Plum Fantasy' is a brighter color with slightly more magenta-red. Other *hibiscus* including: 'Jazzberry Jam' (not patented), 'Tie Dye' U.S. Plant Pat. No. 24,178 and 'Berrylicious' U.S. Plant Pat. No. 24,062 have rippled or pleated petals along the veins and margins but without the puckering of new plant which also give a greater three-dimensional appearance.

*Hibiscus* 'Plum Fantasy' is a unique hardy herbaceous *hibiscus* with the following combined traits:

1. Hardy perennial with dense branching.
2. Many flowers over a prolonged season having vibrant magenta-red overlapping petals and a darker red lustrous eye.
3. Petals have a unique dimpling or puckering giving the appearance of a three-dimensional petals and helping resist strong wind, bright sun and rain conditions.
4. Dark-green, heavily-dissected primarily tri-lobed foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
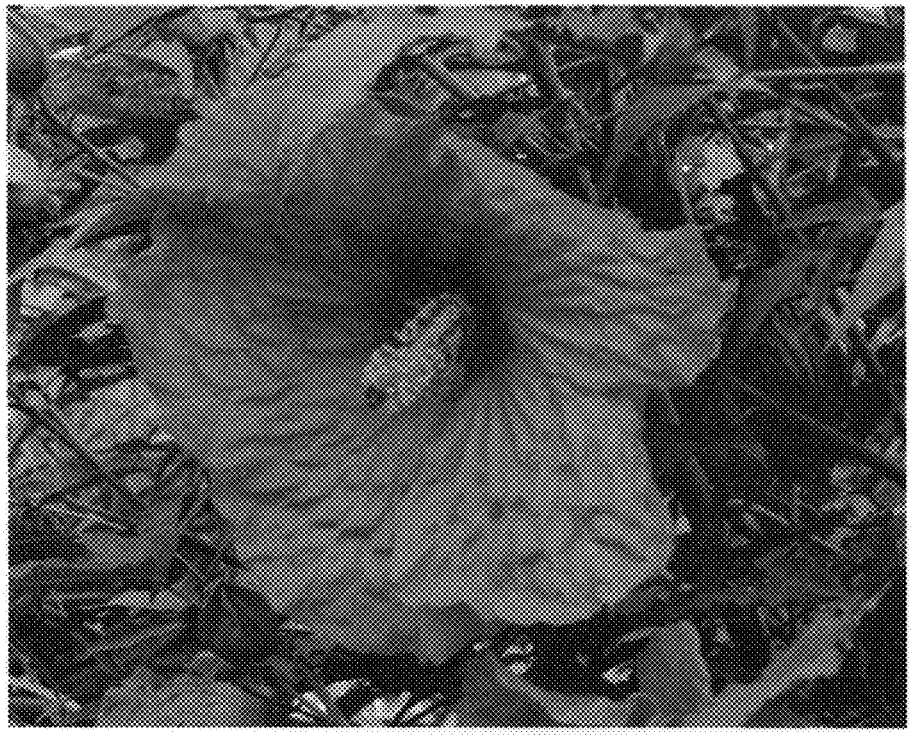
FIG. 1 shows a close-up of the flowers with puckered petals of vibrant magenta-red.
Figure 2:
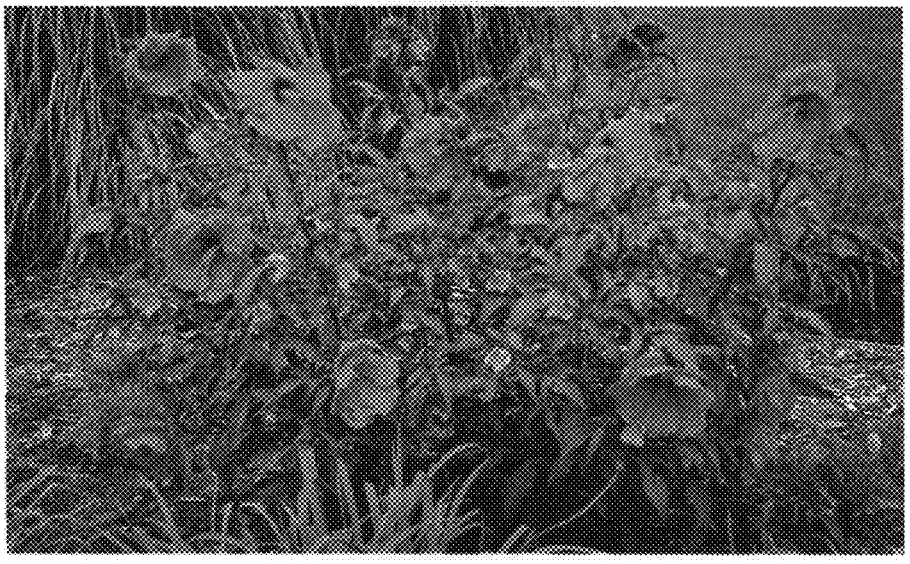
FIG. 2 shows a three-year old plant in the landscape.

The following descriptions and color references are based on the 2001 edition of The Royal Horticultural Society Colour Chart except where common dictionary terms are used. The new plant, *Hibiscus* 'Plum Fantasy', has not been observed under all possible environments. The phenotype may vary slightly with different environmental conditions, such as temperature, light, fertility, moisture and maturity levels, but without any change in the genotype. The following observations and size descriptions are of three year-old plants in the loamy-sand, open-field full-sun trials of a nursery in Zeeland, Mich. with supplemental fertilizer and water as needed. The plants are natural habit and were not treated with plant growth regulators, nor were they pinched at any time in the growth year.

Parentage: *Hibiscus* 'Summer Storm' U.S. Plant Pat. No. 20,443 (female seed parent) times the proprietary hybrid # 05-139-17 (not patented) (male pollen parent).

Propagation:

*Method*.—Stem cuttings and sterile plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant shape and habit*.—Hardy herbaceous perennial with 12 to 16 thick upright and heavily branched main stems producing a upright spreading mound about 165.0 cm tall and 150.0 cm wide, widest about ¾ to top; 7 to 10 primary branches per main stem protruding at 60° to 45° angle from vertical, lateral branches on the lower one third to half of the primary branches; lateral branch size: between 8.0 cm and 25 cm long (shorter at the upper nodes) and average 7.0 mm diameter at the base of branch; flowering on the upper ⅓ of the plant beginning at axillary nodes while still developing at the apex.

*Stem*.—Rounded, glabrous, glaucous; average 165.0 cm tall and 3.5 cm diameter at base; stem color between RHS N186B and RHS N187B.

*Plant size*.—Unpinched plant with stems 165 cm tall; overall plant about 150 cm wide about 35 cm from the top (widest point).

*Internode*.—About 34 nodes per stem, average internode length about 5.0 cm of unpinched plant, varied between 2.0 to 6.0 cm widest in middle portion of stem.

Foliage description: Alternate; dentate; glabrous; mostly deeply cleft tri-lobed; with side lobes at about 80 degree angle from center lobe; texture above lustrous in distal leaves and matte in proximal leaves, texture below matte; leaf blade size average 9.5 cm long and 8.5 cm wide, becoming smaller in distal portion of stem.

*Foliage color*.—Adaxial side darker or more gray than RHS 139A and RHS 136A and more green than RHS N189A with a slight tint of RHS N187B; abaxial side between RHS 147C and RHS 148C.

*Veins*.—Palmate; adaxial primary and secondary adaxial veins mostly nearest RHS 138C and with high sun exposure becoming greyed-purple nearest RHS 183D; primary and secondary abaxial veins nearest RHS 145B with some leaves developing pigment of nearest RHS 187B.

*Petioles*.—Average size 6.5 cm long and 3.0 mm wide; mostly cylindrical with proximal petioles more plano-convex; glaucous, glabrous.

*Petiole color*.—Above between RHS 182B and RHS 183D; and abaxial nearest RHS 143C in more light and where protected from light nearest RHS 139C; below between RHS 187A to RHS 185B where protected from high light intensities.

Flower description:

*Buds*.—One day prior to opening about 7.5 cm long and 3.5 cm in diameter, acute apex and bluntly rounded base, unopened petals wrinkled at veins; exposed petal color between RHS 59C and RHS 60B; prior to showing petals: buds are about 3.5 cm long and 2.5 cm in diameter, ovoid with acute apex, carinate at the sepal fusion seams; color between RHS 141C and RHS 143C rarely with veining, sepal carina having light tinting nearest RHS N186C.

*Epicalyx*.—Entire, smooth, glabrous, linear with sharply acute apex and attenuate base, curved around sepals; typically 11 to 12 per flower; about 2.5 cm long tapering to base of about 3.0 mm wide; adaxial and abaxial color between RHS 141C and RHS 141D.

*Sepals*.—Five, proximal half connate forming campanulate star-shaped calyx; acute apex; margin entire, edentate; about 4.5 cm long and 5.5 cm wide.

*Sepal color*.—Abaxial between RHS 143C and RHS 144B, adaxial color between RHS 144B and RHS 143B.

*Flowers*.—Solitary, 18 to 26 per main stem without pinching; slightly reflexed petals giving color for more than 180 degrees or full front view; upward and outwardly facing; average 22.0 cm across and 5.5 cm deep from outside face to edge of reflexed petals, larger in early part of flowering season; persist for a one to two days; effective for at least 12 weeks beginning mid-July and lasting into October; no detectable fragrance.

*Petals*.—Five; glabrous, slightly lustrous in center and dull both front and back toward middle and perimeter, adnate to the androecium to form a column, imbricate to about 100% overlapping at widest part (petals completely overlapping the next petal to the petal in the position two over), palmately veined, primary and secondary veins impressed on front and ribbed on back; shape: rounded; margins: entire, edentate; apex: rounded; base: short claw-like; size: average 12 cm long and 13 cm wide at widest portion (larger in earlier part of flowering season); center dark eye about 5.0 cm diameter.

*Petal color*.—Adaxial between RHS 59C and RHS 61B with a darker eye of darker than RHS 59A, nearest RHS 187A; abaxial color between RHS 59C and RHS 61C; vein color nearest RHS 187C radiating out from the center eye about 2.5 cm on adaxial surface and the same as surrounding tissue on abaxial surface.

*Gynoecium*.—Style: enclosed in column about 7.5 cm long and 1.5 cm wide at base; column color blending between RHS 52A and RHS N66A at middle and base, nearest RHS 63A distally; style protruding from column and split in distal 8.0 mm portion into typically five branches and protrudes from column, branch diameter 2.0 mm; branch color nearest RHS 187C. Stigma: typically five; globose, puberulose, about 3.0 mm in diameter, nearest RHS 187B. Ovary: superior, about 6.0 mm across at base and 6.0 mm tall; acute apex; color between RHS 145B and RHS 145C.

*Androecium*.—Filaments: numerous, about 140; less than 1.0 mm in diameter and about 6.0 mm long; attached along nearly the entire length of column; color between RHS 64B and RHS 64A. Anthers: reniform; about 2 mm long and 1 mm wide; nearest RHS 186B. Pollen: numerous, globose, less than 0.1 mm long, between RHS 156C and RHS 161C.

*Pedicel*.—Rounded in cross section, glabrous; length from base of sepal to abscission point average 2.2 cm long and 3.0 mm wide, longer on early flowers decreasing in distal flowers; color nearest RHS 138B.

*Peduncle*.—Rounded, glabrous, flowers are held easily visible on average 5.5 cm long from abscission point to stem and 3.0 mm wide, longer on earlier flowers; color nearest RHS 138A with tinting of RHS 186A in higher direct sun exposure.

*Fruit*.—Few, loculicidal capsule; glabrous; globose, occasionally with abruptly acute apex; color between RHS N199B and RHS N199C when mature.

*Seed*.—Minutely floccose, typically globose; about 3.0 mm in diameter; color between RHS 200A and RHS N199B.

Resistance: The flowers of 'Plum Fantasy' have resisted wind, rain and hot sun conditions better than most hardy perennial *hibiscus*. Other pest and disease resistance beyond that of other hardy perennial *hibiscus* cultivars has not been observed. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Plum Fantasy' as herein illustrated and described, suitable for potted plant culture, landscaping as a specimen or en masse, and especially suited for patios and confined spaces because of the compact habit.

* * * * *